(12) United States Patent
Sweeney

(10) Patent No.: US 9,603,644 B2
(45) Date of Patent: Mar. 28, 2017

(54) METHODS AND DEVICES FOR DELIVERY OF MEDICINE TO BONE

(75) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 1010 days.

(21) Appl. No.: 13/569,062

(22) Filed: Aug. 7, 2012

(65) Prior Publication Data

US 2014/0046379 A1 Feb. 13, 2014

(51) Int. Cl.
| A61B 17/86 | (2006.01) |
| A61B 17/34 | (2006.01) |
| A61B 17/70 | (2006.01) |
| A61F 2/30  | (2006.01) |

(52) U.S. Cl.
CPC .......... *A61B 17/864* (2013.01); *A61B 17/863* (2013.01); *A61B 17/8685* (2013.01); *A61B 17/3472* (2013.01); *A61B 17/7098* (2013.01); *A61F 2002/30677* (2013.01)

(58) Field of Classification Search
CPC ....... A61B 17/84; A61B 17/86; A61B 17/863; A61B 17/864
USPC .......................................... 606/304, 311–316
See application file for complete search history.

(56) References Cited

U.S. PATENT DOCUMENTS

| 3,310,051 A | 3/1967  | Schulte |
| 4,399,814 A | 8/1983  | Pratt et al. |
| 4,464,178 A | 8/1984  | Dalton |
| 4,653,487 A | 3/1987  | Maale |
| 4,653,489 A | 3/1987  | Tronzo |
| 4,760,844 A | 8/1988  | Kyle |
| 4,772,261 A | 9/1988  | Von Hoff et al. |
| 4,976,692 A | 12/1990 | Atad |
| 5,047,030 A | 9/1991  | Draenert |
| 5,122,114 A | 6/1992  | Miller et al. |
| 5,203,770 A | 4/1993  | Wigness et al. |
| 5,372,583 A | 12/1994 | Roberts et al. |
| 5,380,319 A | 1/1995  | Saito et al. |
| 5,425,723 A | 6/1995  | Wang |
| 5,562,625 A | 10/1996 | Stefancin, Jr. |
| 5,618,286 A | 4/1997  | Brinker |
| 5,681,289 A | 10/1997 | Wilcox et al. |
| 5,702,372 A | 12/1997 | Nelson |
| 5,749,883 A | 5/1998  | Halpern |

(Continued)

FOREIGN PATENT DOCUMENTS

| EP | 0 858 775 | 8/1998 |
| EP | 1 653 869 | 6/2011 |

(Continued)

OTHER PUBLICATIONS

U.S. Appl. No. 12/427,520, filed Apr. 21, 2009, Patrick J. Sweeney.

(Continued)

*Primary Examiner* — Matthew Lawson
(74) *Attorney, Agent, or Firm* — Foley & Lardner LLP

(57) ABSTRACT

A bone screw includes a shaft, a cannulated portion formed in the shaft, and a fenestration in the shaft connecting the cannulated portion to an exterior of the bone screw. A wall between the cannulated portion and the exterior of the bone screw includes a first wall portion having a different thickness than a second wall portion.

5 Claims, 8 Drawing Sheets

(56) References Cited

U.S. PATENT DOCUMENTS

| | | |
|---|---|---|
| 5,752,941 A | 5/1998 | Romano' et al. |
| 5,800,407 A | 9/1998 | Eldor |
| 5,871,484 A | 2/1999 | Spievack et al. |
| 5,951,160 A | 9/1999 | Ronk |
| 6,019,761 A | 2/2000 | Gustilo |
| 6,048,343 A | 4/2000 | Mathis et al. |
| 6,077,265 A | 6/2000 | Werding et al. |
| 6,210,376 B1* | 4/2001 | Grayson ............. A61B 17/3472 604/264 |
| 6,214,012 B1 | 4/2001 | Karpman et al. |
| 6,220,888 B1 | 4/2001 | Correa |
| 6,228,088 B1 | 5/2001 | Miller et al. |
| 6,364,856 B1 | 4/2002 | Ding et al. |
| 6,387,098 B1 | 5/2002 | Cole et al. |
| 6,461,327 B1 | 10/2002 | Addis et al. |
| 6,679,890 B2 | 1/2004 | Margulies et al. |
| 7,527,611 B2 | 5/2009 | Sweeney |
| 7,575,572 B2 | 8/2009 | Sweeney |
| 7,608,062 B2 | 10/2009 | Sweeney |
| 8,057,090 B1 | 11/2011 | Saha et al. |
| 8,062,270 B2 | 11/2011 | Sweeney |
| 2001/0021852 A1 | 9/2001 | Chappius |
| 2002/0138146 A1 | 9/2002 | Jackson |
| 2003/0045885 A1 | 3/2003 | Margulies et al. |
| 2003/0083662 A1 | 5/2003 | Middleton |
| 2003/0139751 A1 | 7/2003 | Evans et al. |
| 2003/0212426 A1 | 11/2003 | Olson et al. |
| 2004/0225292 A1* | 11/2004 | Sasso ................. A61B 17/8615 606/916 |
| 2005/0015059 A1 | 1/2005 | Sweeney |
| 2005/0015060 A1 | 1/2005 | Sweeney |
| 2005/0059972 A1* | 3/2005 | Biscup ................ A61B 17/686 606/308 |
| 2006/0079905 A1 | 4/2006 | Beyar et al. |
| 2006/0111767 A1 | 5/2006 | Olson et al. |
| 2007/0073295 A1* | 3/2007 | Biedermann .......... A61B 17/68 606/62 |
| 2007/0083265 A1 | 4/2007 | Malone |
| 2008/0039846 A1 | 2/2008 | Lee et al. |
| 2008/0039855 A1 | 2/2008 | Lambert |
| 2009/0164016 A1 | 6/2009 | Georgy et al. |
| 2009/0204158 A1 | 8/2009 | Sweeney |
| 2010/0042213 A1 | 2/2010 | Nebosky et al. |
| 2010/0106199 A1* | 4/2010 | Sawa ................. A61B 17/7098 606/304 |
| 2010/0131014 A1 | 5/2010 | Peyrot et al. |
| 2010/0262089 A1 | 10/2010 | Sweeney |
| 2011/0046682 A1* | 2/2011 | Stephan ............... A61B 17/686 606/305 |

FOREIGN PATENT DOCUMENTS

| | | |
|---|---|---|
| WO | WO-02/098307 A1 | 12/2002 |
| WO | WO-2005/009258 | 2/2005 |
| WO | WO-2010/019788 | 2/2010 |

OTHER PUBLICATIONS

U.S. Appl. No. 13/227,230, filed Sep. 7, 2011, Patrick J. Sweeney.
U.S. Appl. No. 13/270,072, filed Oct. 10, 2011, Patrick J. Sweeney.
Cecil, M.L. et al., "Projection of the S2 Pedicle Onto the Posterolateral Surface of the Ilium—A Technique for Lag Screw Fixation of Sacral Fractures or Sacroiliac Joint Dislocations," Spine 1996, vol. 21, pp. 875-878, www.kalindra.com/project.htm, 6 pages.
European Office Action for Application No. 04757057.7, dated Jan. 26, 2010, 5 pages.
European Search Report for European Patent Application No. 04757057.7, mailed Jul. 2, 2010, 4 pages.
European Search Report for European Patent Application No. 04757057.7, mailed Nov. 30, 2009, 3 pages.
European Search Report for European Patent Application No. 11250603.5-2310, dated Sep. 29, 2011, 6 pages.
Press release from Spine Center Atlanta, "New Screw Debut First-time Use for New Spinal Surgery Device," 2002, Orthopaedic & Spine Surgery of Atlanta, LLC. www.SpineCneterAtlanta.com, 2 pages.
Sato, T. et al., "Calcium Phosphate Augmentation of Screw Fixation in Femoral Neck Fracture," 47th Annual Meeting, Orthopaedic Research Society, Feb. 25-28, 2001, San Francisco, CA, 1 page.
International Search Report and Written Opinion for International Application No. PCT/US2014/035542, dated Sep. 22, 2014, 14 pages.
International Search Report and Written Opinion for PCT Application PCT/US2013/052853, dated Jan. 14, 2014, 15 pages.
Communication received in European Patent Application No. 11250603.5, dated Feb. 20, 2015, 5 pages.
International Search Report and Written Opinion for PCT Application No. PCT/US2015/014216, dated Apr. 22, 2015, 14 pages.
Communication received in European Patent Application No. 11250603.5, dated Mar. 11, 2016, 6 pages.

* cited by examiner

METHODS AND DEVICES FOR DELIVERY OF MEDICINE TO BONE

BACKGROUND

The present invention relates to devices for delivering substances such as medicants to bones. More particularly, the present invention concerns devices and related methods for delivering substances to the interior or exterior of fractured or otherwise injured bones, especially to the fracture interface.

Delivery of medicants or therapeutics to bones is an often desirable but difficult-to-achieve process, especially if one desires to focus the delivery to the interior of a bone or to a particular area in a bone. Delivery pins or needles are sometimes used to deliver medication or other fluids into bone. Such pins are typically made of metals such as titanium or steel, and must be fabricated ahead of time for later use. Thus, it is difficult to customize the pins for directing the delivery of medicants or fluids to a specific area of interest within a bone. Moreover, such pins do not serve as fixation screws for holding two or more bones or bone pieces in a fixed spatial relationship with respect to each other.

Bone screws can be used to repair or strengthen fractured or otherwise damaged or diseased bones, often by fixing two or more bones or bone pieces with respect to each other, in which case the bone screw may be referred to as a fixation screw. Such screws have been adapted to deliver liquids such as bone cements to the interior of a bone. These devices must be fabricated ahead of time for later use, thereby substantially limiting the ability to customize the device to the needs of an individual patient. Moreover, while these devices may be suitable for the one-time delivery of a curable substance such as a bone cement, they provide no way to control or regulate the amount of substance delivered. Substance delivery also cannot be directed to certain areas within the bone and not others without changing the location or configuration of the bone screw itself.

SUMMARY

One embodiment of the invention relates to a bone screw including a shaft having a wall, a cannulated portion formed in the shaft, and a fenestration in the shaft connecting the cannulated portion to an exterior of the bone screw. The wall between the cannulated portion and the exterior of the bone screw includes a first wall portion having a different thickness than a second wall portion.

Another embodiment of the invention relates to a bone screw, including a shaft, a cannulated portion formed in the shaft, a fenestration in the shaft providing an opening between the cannulated portion and an exterior of the bone screw, and an edge along a surface of the shaft defining the fenestration.

Still another embodiment of the invention relates to a method of delivering medicine to bone. The method includes implanting a bone screw into a bone, placing an insert into a hollow portion of the bone screw, and delivering a medication into the insert. The method further includes removing the insert from the bone screw and placing an occluding shaft into the hollow portion of the bone screw.

It is to be understood that both the foregoing general description and the following detailed description are exemplary and explanatory only, and are not restrictive of the invention as claimed.

BRIEF DESCRIPTION OF THE DRAWINGS

Features, aspects, and advantages of the present invention will become apparent from the following description, appended claims, and the accompanying exemplary embodiments shown in the drawings, which are briefly described below.

DETAILED DESCRIPTION

Figure 1:
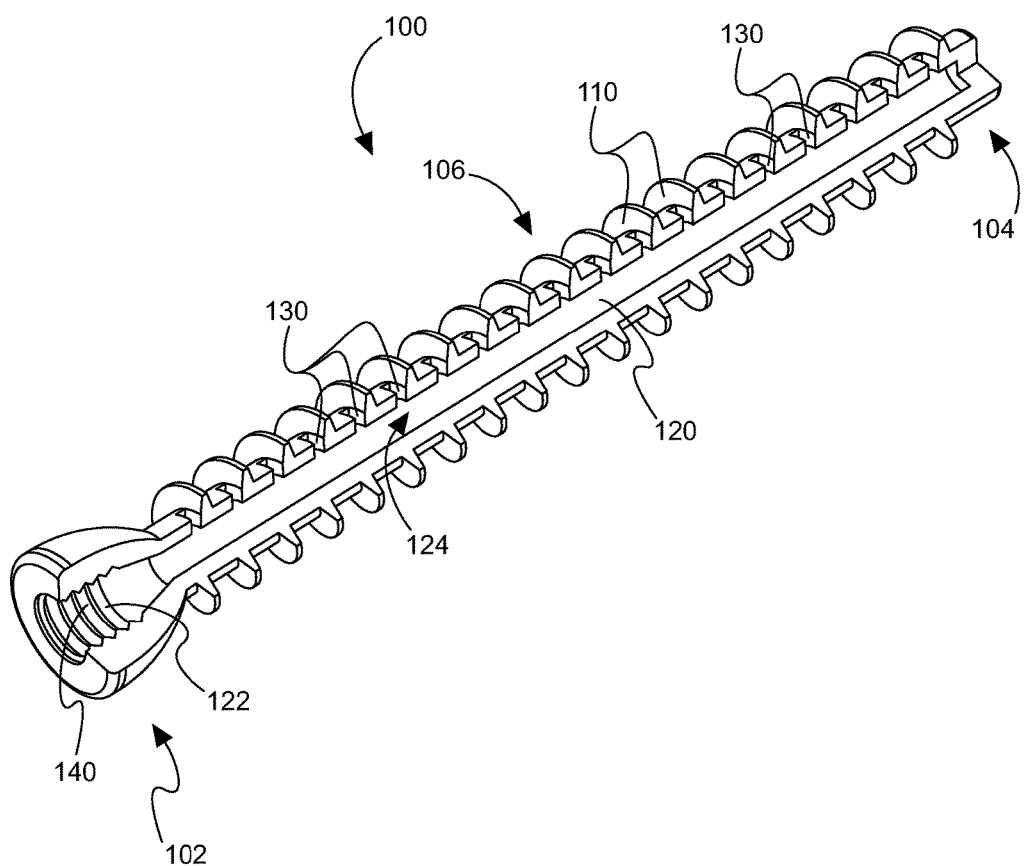
FIG. 1 is a perspective view of a bone screw, in accordance with an exemplary embodiment.

For the purposes of this description, the term "cannulated" means that the described device or component (e.g., screw or insert) includes a hollow cavity disposed inside at least part of its shaft. For example, the cavity may consist of a bore beginning at or near one end of the screw or insert and extending longitudinally into the screw or insert. Other configurations are possible, however, and the hollow cavity need not be restricted to a cylindrical shape or a circular cross-section. The cavity may extend throughout the entire length of the screw or insert, thus creating openings at each end of the screw or insert, or alternatively, the cavity may extend only partially into the interior of the screw or insert. The shape and size of the cavity may be suitably chosen to allow delivery of the desired substance through the screw or insert to the bone area of interest. When it is desired to use the cannulated portion of the screw or insert as reservoir for the substance to be delivered, for example, the cavity may be made as large as possible so long as the screw and insert maintain the structural integrity needed for introduction into the bone.

For the purposes of this description, the term "fenestration" is used broadly to include any slot, gap, or perforation that defines an opening between the inside of the cannulated portion of the screw or insert to the outside of the screw or insert whereby a desired substance may be delivered. Thus, a fenestrated screw includes an opening which defines a substance delivery pathway between the internal cannulated portion and the exterior of the screw. Likewise, a fenestrated insert is one that includes an opening which defines a substance delivery pathway between the internal cannulated portion and the exterior of the insert. In certain embodiments of the present invention where a fenestrated insert is utilized in combination with a fenestrated screw, at least one screw fenestration and at least one insert fenestration may be designed to align with each other once the screw and insert are in their appropriate configuration and position. Alignment or coordination of an insert fenestration and a screw fenestration will define a substance delivery pathway between the internal cannulated portion of the insert and the exterior of the screw.

For the purposes of this description, the term "bone screw" is intended to refer to screws of all types which are presently known or hereafter devised for implantation into bone. In this regard, cancellous screws, cortical screws, and machine screws are all contemplated as being within the scope of the types of screws useful in the practice of selected embodiments of the present invention. The bone screws described herein will typically include threads along at least a portion of the exterior of the screw shaft, but it should be appreciated that tacks, pins, nails and the like may also be included within the definition of a bone screw for the purposes of this description, whether threaded or unthreaded. When threads are present, it may be found advantageous to use self-tapping threads, or alternatively, the threads can be pre-cut in the bone prior to bone screw insertion.

Referring now to FIG. 1, in accordance with an exemplary embodiment, a bone screw 100 has two ends 102 and 104 connected by a shaft 106, and bone screw threads 110. The cut-out of FIG. 1 reveals that bone screw 100 includes a hollow, cannulated portion 120, and one or more bone screw fenestrations 130 along the length of the cannulated portion 120. The cannulated portion 120 (e.g., lumen, hollow, chamber, etc.) may be formed by a longitudinal bore 124 through the shaft 106. The longitudinal bore forming the cannulated portion of a bone screw may be formed with a drilling operation (e.g., gun drilling).

It will be appreciated by one skilled in the art that the fenestrations 130 need not be even spaced along the cannulated portion 120, but may be arranged in a desired pattern or frequency along the length of the cannulated portion 120. The fenestrations 130 may extend along a circumference of the bone screw 100 or may extend in a longitudinal direction along the length of the bone screw 100. It will be further appreciated by one skilled in the art that one end 122 of the cannulated portion 120 of the bone screw 100 is configured to accept a bone screw insert. For example, the bone screw 100 may comprise additional threads 140 on the one end 122 of the cannulated portion 120 to promote fixation of a bone screw insert.

Figure 4:
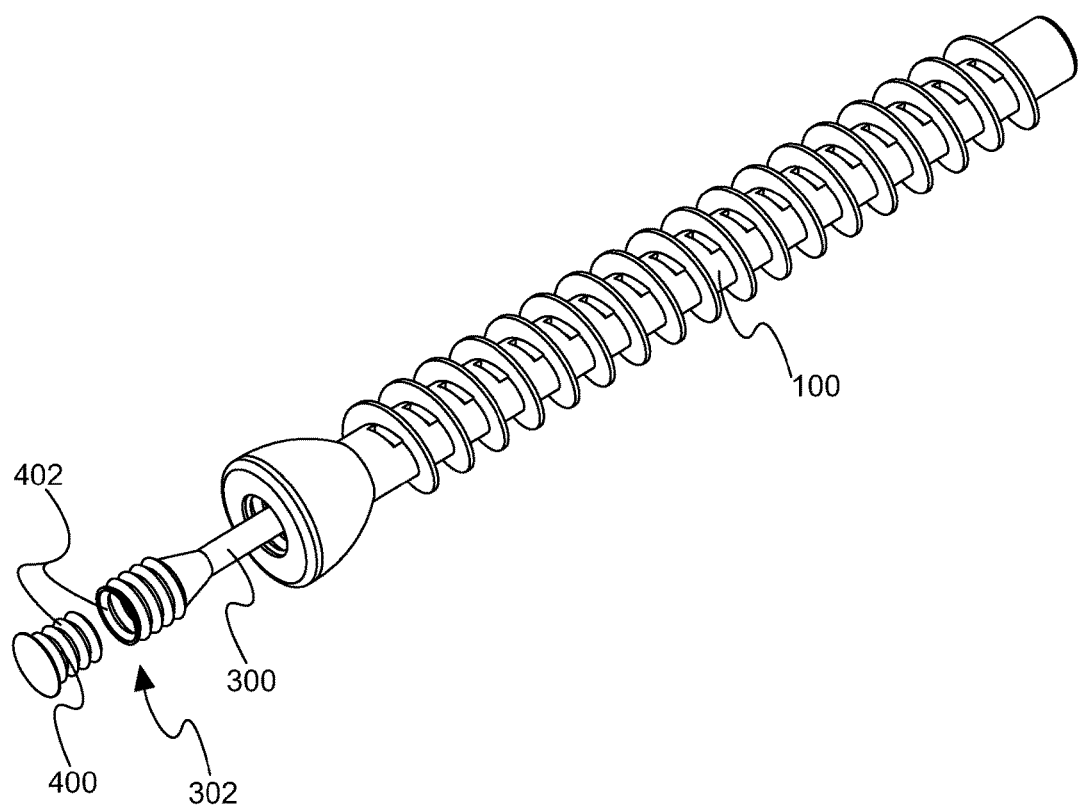
FIG. 4 is a perspective view of a bone screw, a bone screw insert, and an insert cap, in accordance with an exemplary embodiment.

The cannulated portion 120 of the bone screw 100 may be coaxial with the shaft 106 (e.g., with the longitudinal axis of the bore 124 being collinear with the longitudinal axis of the shaft 106) as shown in FIGS. 1 and 4 and the wall of the shaft 106 may be a consistent thickness about the circumference of the shaft 106 at any point along the length of the shaft 106 between the first end 102 and the second end 104.

In one embodiment, the bone screw may be a fixation screw used to hold two or more bones or bone pieces in a fixed spatial relationship with respect to each other. The bone screw may be used to mend peripheral skeletal fractures or osteotomies, repair a spondyloysis or an odontoid fracture, or fuse lumbar facet joints, for example. Other beneficial uses of bone screws, and more particularly, fixation screws, will be known to one skilled in the art and are to be included within the scope of this application.

The bone screw 100 may include any material suitable for placement into a bone without harmful effects on the patient. Examples of suitable materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalciumphosphate. Other materials useful for bone screw construction will be known to those skilled in the art.

Figure 2:
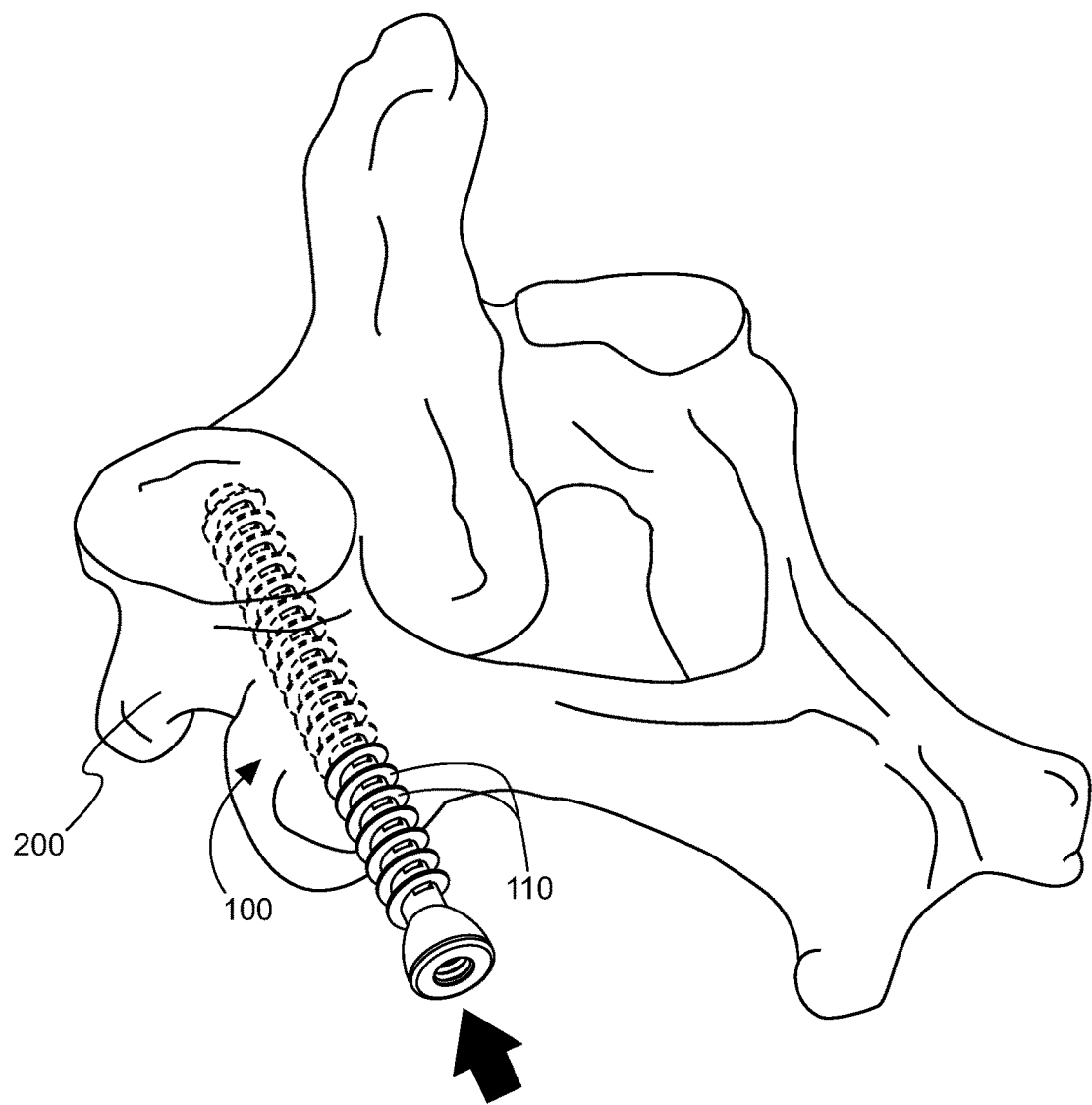
FIG. 2 is a perspective view of the bone screw of FIG. 1 inserted into the hip bone of a patient.

Referring now to FIG. 2, a bone screw 100 is shown disposed partially within a bone 200. Bone 200 may, for example, be a human hip bone. In one embodiment, bone screw 100 is disposed within bone 200 by rotating the bone screw 100 such that the bone screw threads 110 act to pull bone screw 100 into bone 200, thereby anchoring bone screw 100 into place.

Figure 3A:
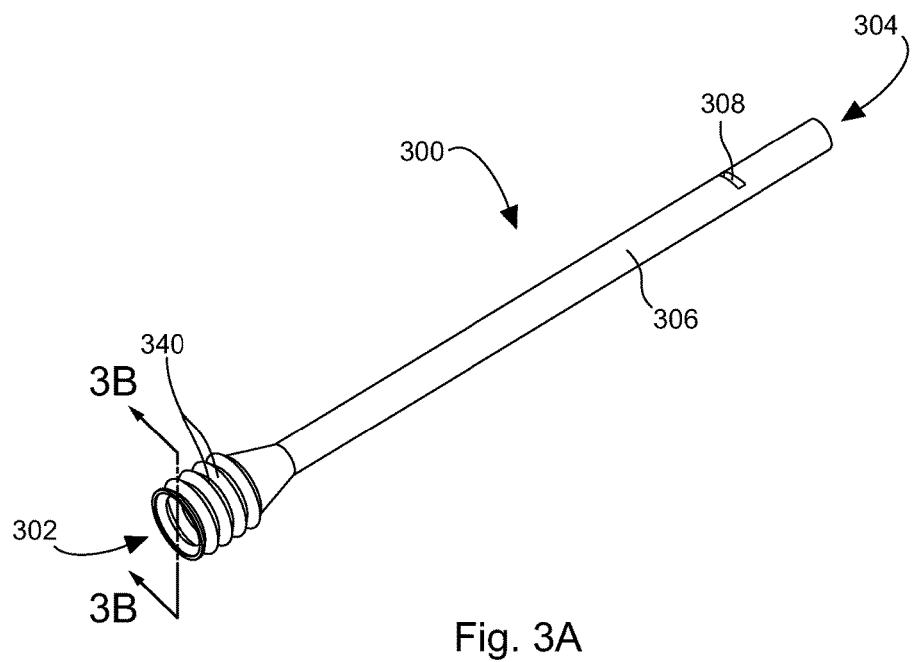
FIG. 3A is a perspective view of a bone screw insert with a single fenestration, in accordance with an exemplary embodiment.
Figure 3B:
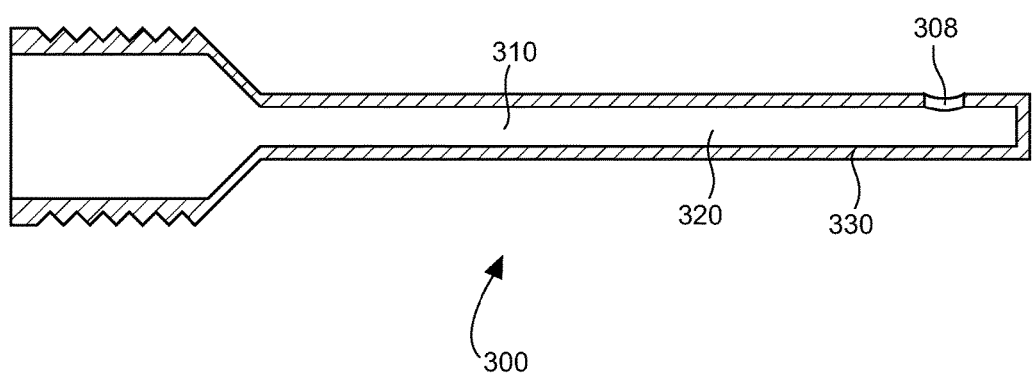
FIG. 3B is a schematic cross-sectional view of the bone screw insert of FIG. 3A.

For the purposes of this description, the term "insert" is used to refer to one or more cannulated members which are disposed within the cannulated portion of a bone screw. Referring now to FIGS. 3A and 3B, in accordance with an exemplary embodiment, an insert 300 includes a cannulated portion 310 with a hollow cavity 320 surrounded by an insert wall 330, where the cavity and wall dimensions may be suitably chosen in order to carry out the practice of the concepts disclosed herein. In certain embodiments, the insert may include a single piece, as disclosed in FIGS. 3A and 3B. When the insert 300 is a single piece, the insert includes two ends, 302 and 304, connected by a shaft 306. Alternatively, the insert may include two or more pieces or sections that, when taken together, form the insert. The shaft may be cannulated along its entire length, creating openings at each end of the insert. Alternatively, the cannulation may extend only partially into the shaft so long as the cannulation is sufficient to allow for delivery of a substance from one end of the insert to one or more bone screw fenestrations. One end 302 of the insert 300 may include threads 340 which interlock with bone screw threads 140 of FIG. 1 to help fix an insert 300 into a bone screw 100. When the insert includes two or more pieces or sections, only one of the sections need be cannulated such that the insert sections, when taken together, allow for delivery of a substance from one end of the insert to one or more bone screw fenestrations.

In some embodiments disclosed herein, the insert 300 is cannulated and has a single passage or fenestration 308 for communication of fluids. When substantially unimpeded delivery of a substance to one or more bone screw fenestrations is desired, the insert may include multiple insert fenestrations. An insert having an appropriate number, size, shape, and location of insert fenestrations can be chosen by the practitioner to provide a delivery pathway between at least one end of the insert and the one or more bone screw fenestrations. For example, the insert 300 may include a plurality of insert fenestrations 308 having a substantially rectangular cross-section. Alternatively, the delivery pathway may initiate at one end of the bone screw and pass through the insert to one or more bone screw fenestrations. The insert fenestrations need not match the bone screw fenestrations in number, size, shape, or location, although it may be advantageous to locate at least one of the insert fenestrations such that it may be substantially aligned with at least one bone screw fenestrations once both the bone screw and the insert are in place. Various embodiments of the insert and related bone screws are shown in U.S. application Ser. No. 13/227,230 titled "Method and Device for Delivering Medicine to Bone," filed Sep. 7, 2011, which is incorporated herein by reference in its entirety.

Alternatively, fluid may be communicated through a portion of the wall 330 that is permeable to the substance to be delivered such that the substance is delivered to the exterior of the insert by diffusion through the insert wall or through small openings in the insert wall. Such openings may be intentionally created such as by increasing the porosity of the insert material (e.g., by introducing a series of pinpricks into the material), or they may exist naturally as pores in the material. When the insert includes a material that is at least partially permeable to the substance to be delivered, the insert may or may not be fenestrated so long as delivery of the desired substance is not completely impeded by the insert. An embodiment including a permeable but non-fenestrated insert may be preferred when it is desired to effect a controlled, slow release of the desired substance to a bone, or when it is desired to prevent bone fragments, blood, fat or other materials or fluids from traveling from the exterior of the insert to the interior cavity.

While in some embodiments disclosed herein the insert 300 is cannulated and has a single passage for communication of fluids, in other embodiments the insert may include a second conduit for suction of fluids after irrigation. As such, one passage may provide fluid while the other passage concurrently removes fluid. Following irrigation, the insert may be removed and a bone screw may then be inserted into the irrigated opening in the bone. The same insert or another insert, may then be inserted into bone screw to deliver medications or other fluids. Such a process may be particularly beneficial for treating open long-bone fractures.

In an exemplary embodiment, the exterior dimensions of the insert 300 are only slightly smaller than the interior dimensions of the cannulated bone screw 100 to provide for a tight but sliding fit when the insert 300 is placed into the bone screw 100, as depicted in FIG. 4 in which the insert 300 is shown partially disposed within the bone screw 100. Also disclosed in FIG. 4 is an insert cap 400 which can be used to substantially seal the one end 302 of the insert 300 via insert cap threads 402 either before, during, or after the bone screw 100 and insert 300 are put into place. The insert 300 may have substantially the same cross-sectional shape as the cannulated portion 120 of the bone screw 100, or their cross-sectional shapes may be different. For example, the internal bone screw cavity and the exterior surface of the insert may have a substantially circular cross-section. One advantage of this embodiment is that after the insert has been disposed within the bone screw, the insert may be rotated with respect to the screw to achieve alignment of certain of the insert and bone screw fenestrations, for example. In another embodiment, the insert and bone screw may have substantially non-circular cross-sections such that the insert is not free to rotate once it has been disposed within the bone screw. In yet another embodiment, at least part of the insert cross-section may not match that of the bone screw cavity such that when the insert is disposed within the bone screw, one or more channels are formed longitudinally along at least part of the insert and bone screw shafts. Such channels may be useful, for example, to allow air or fluids to escape the bone screw cavity as the insert is introduced.

The inserts described herein may be formed of any material compatible with the bone screw and able to be placed within the bone screw without producing adverse effects to the patient. Examples of suitable insert materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalciumphosphate. Other materials useful for insert construction will be known to those skilled in the art. When the insert includes two or more sections, the sections need not be formed of the same material. In addition, when it is desired that the insert be permeable to the substance to be delivered, one or more of the insert sections may be formed of a material specifically chosen to impart the desired level of permeability to the insert.

Figure 5A:
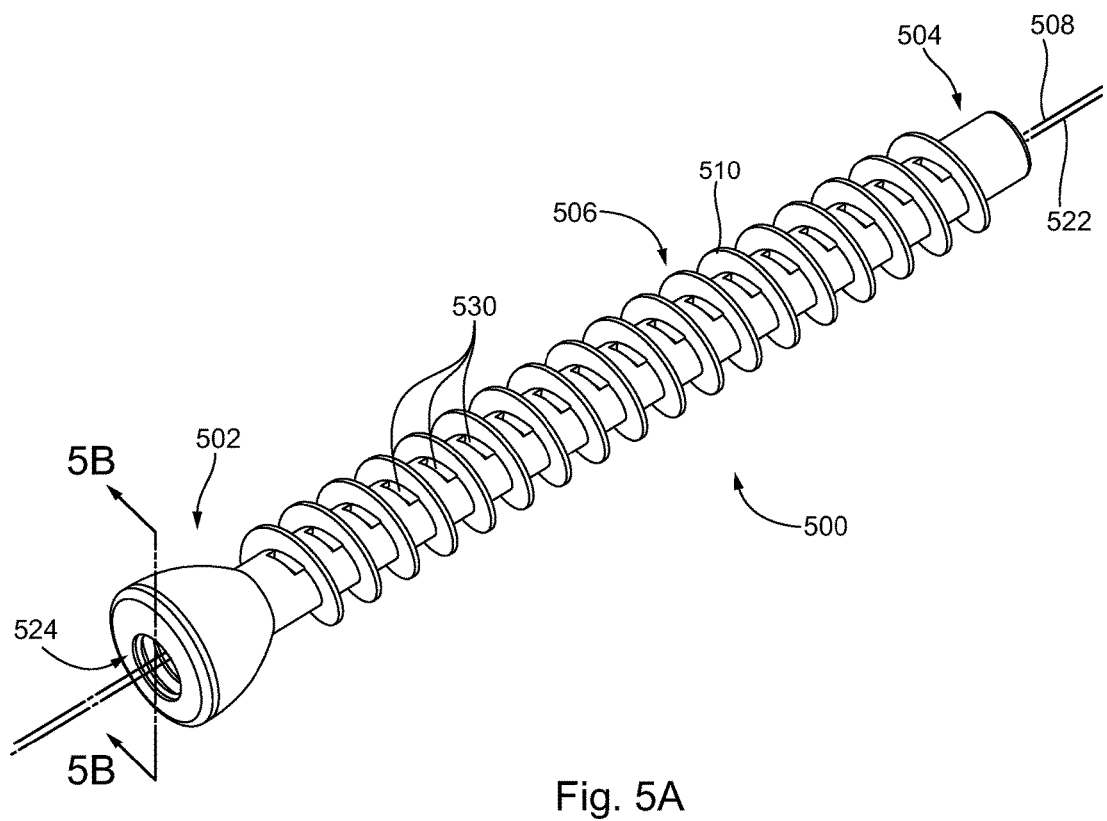
FIG. 5A is a perspective of a bone screw with an off-center cannulated portion, in accordance with an exemplary embodiment.
Figure 5B:
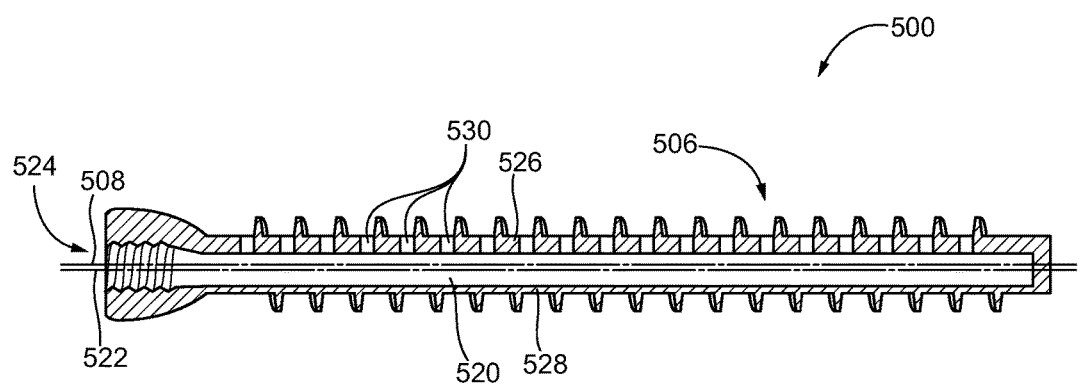
FIG. 5B is a schematic cross-sectional view of the bone screw of FIG. 5A.

Referring now to FIGS. 5A and 5B, in another embodiment, a bone screw 500 may have an off-center cannulated portion. The bone screw 500 has two ends 502 and 504 connected by a shaft 506, and bone screw threads 510. The bone screw 500 further includes a hollow, cannulated portion 520, and one or more bone screw fenestrations 530 along the length of the cannulated portion 520. In one embodiment, the fenestrations 530 may be provided on only one side of the bone screw 500. The fenestrations 530 provides an opening or passage between the hollow cannulated portion 520 of the bone screw 500 the exterior of the bone screw 500. The cannulated portion 520 may be formed by a longitudinal bore 524 (e.g., hollow, chamber, etc.) through the shaft 506. The longitudinal axis 522 of the bore 524 may be offset from and parallel to the longitudinal axis 508 of the shaft 506, such that the cannulated portion 520 is not coaxial with the shaft 506. The wall of the shaft 506 surrounding the hollow cannulated portion 520 may therefore have a thickness that varies about the circumference of the shaft 506 with a thicker first wall portion 526 and a thinner second wall portion 528. As shown in FIGS. 5A and 5B, in one embodiment, the fenestrations 530 may be provided in the first wall portion 526 with the increased thickness of the first wall portion 526 adding strength to the shaft 506 to compensate for the reduction in strength introduced by the fenestrations 530. However, in other embodiments, the fenestrations 530 may be provided in the second wall portion 528.

Figure 6A:
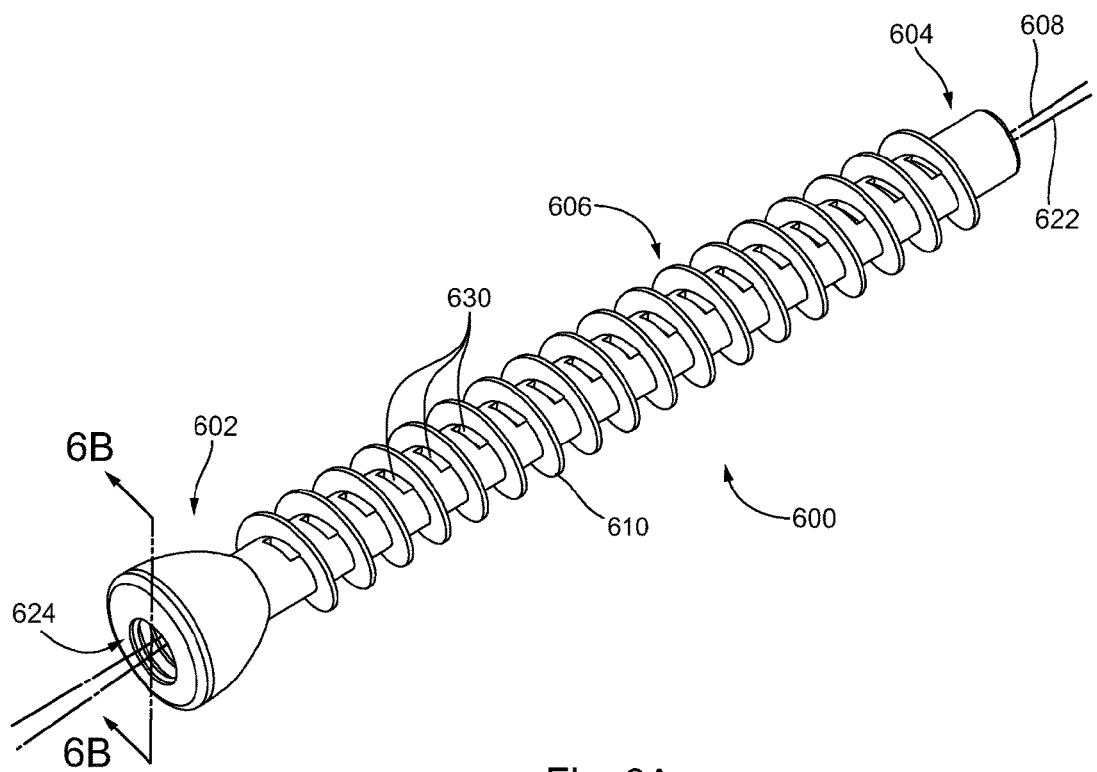
FIG. 6A is a perspective of a bone screw with an angled cannulated portion, in accordance with an exemplary embodiment.
Figure 6B:
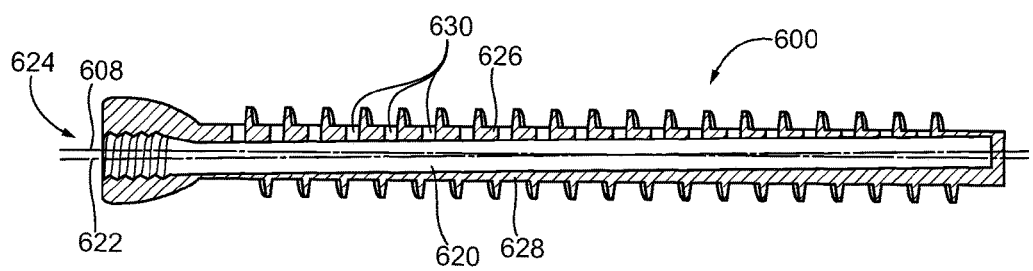
FIG. 6B is a schematic cross-sectional view of the bone screw of FIG. 6A.

Referring now to FIGS. 6A and 6B, in another embodiment, a bone screw 600 may have an angled cannulated portion. The bone screw 600 has two ends 602 and 604 connected by a shaft 606, and bone screw threads 610. The bone screw 600 further includes a hollow, cannulated portion 620, and one or more bone screw fenestrations 630 along the length of the cannulated portion 620. The cannulated portion 620 may be formed by a longitudinal bore 624 (e.g., hollow, chamber, etc.) through the shaft 606. The longitudinal axis 622 of the bore 624 may be oriented relative to the longitudinal axis 608 of the shaft 606, such that the cannulated portion 620 is not coaxial with the shaft 606. Further, the longitudinal axis 622 of the bore 624 may be angled relative to the longitudinal axis 608 of the shaft 606. The wall of the shaft 606 surrounding the hollow cannulated portion 620 may therefore have a thickness that varies about the circumference of the shaft 606 with a first wall portion 626 and a second wall portion 628. Because the bore 624 is angled, the thickness of the first wall portion 626 and the second wall portion 628 each vary along the length of the shaft 606.

Figure 7A:
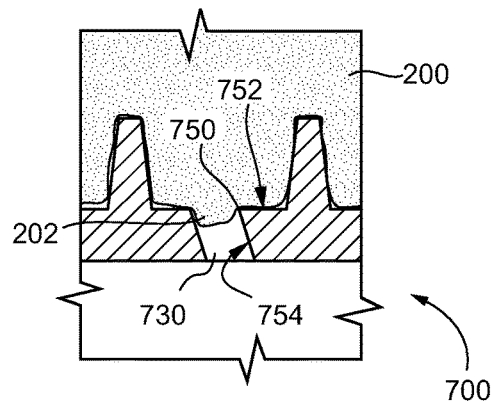
FIG. 7A is a detail schematic cross-sectional view of a fenestration for a bone screw with a sharpened edge, in accordance with an exemplary embodiment.
Figure 7B:
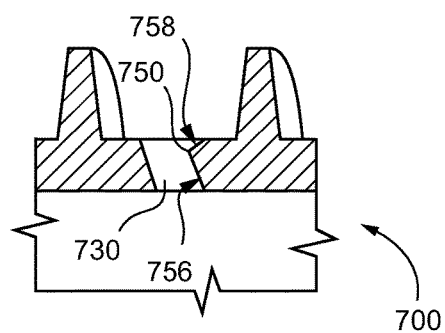
FIG. 7B is a detail schematic cross-sectional view of a fenestration for a bone screw with a sharpened edge, in accordance with another exemplary embodiment.
Figure 7C:
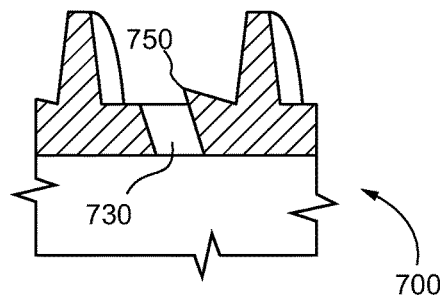
FIG. 7C is a detail schematic cross-sectional view of a fenestration for a bone screw with a sharpened edge, in accordance with another exemplary embodiment.
Figure 7D:
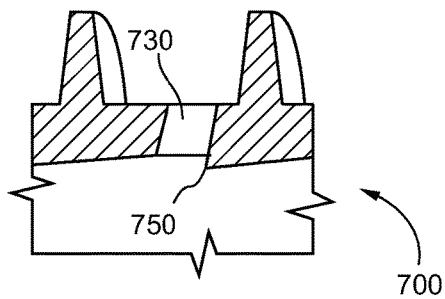
FIG. 7D is a detail schematic cross-sectional view of a fenestration for a bone screw with a sharpened edge, in accordance with another exemplary embodiment.

Referring now to FIGS. 7A-7E, a bone screw 700 may include fenestrations 730 having edges (e.g. sharpened or tapered sides), shown as edge 750 in various embodiments in FIGS. 7A-7E. As shown in FIG. 7A, during the period in which the bone screw 700 is inserted into a bone 200, growth 202 of the bone 200 may intrude into the openings formed in the wall of the bone screw 700 by the fenestrations 730. The edge 750 is configured to assist in removing the bone screw 700 from the bone 200 by cutting through growth 202 in or proximate to the fenestration 730. The edge 750 may be formed by the exterior surface 752 of the screw 700 and a surface 754 of the fenestration 730. The fenestration 730 may be a slot extending along a circumference of the bone screw 700 and the fenestration surface 752 may be at an acute angle relative to the exterior surface 754 (see FIG. 7A). In another embodiment, the edge 750 may be formed inside the fenestration 730 between a first surface 756 extending from the hollow cannulated portion of the bone screw 700 and a second surface 758 extending from the exterior of the bone screw 700 (see FIG. 7B). In another embodiment, the edge 750 may protrude past the exterior of the bone screw 700 (see FIG. 7C) or the edge 750 may protrude into the hollow cannulated portion of the bone screw 700 (see FIG. 7D).

Figure 7E:
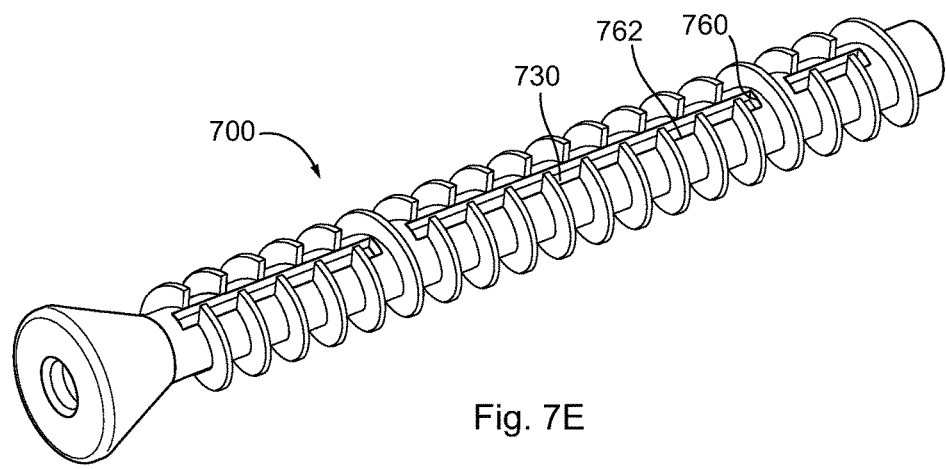
FIG. 7E is a detail schematic cross-sectional view of a fenestration for a bone screw with a sharpened edge, in accordance with another exemplary embodiment.

Referring to FIG. 7E, in another embodiment, the fenestration 730 may be a slot extending longitudinally along a length of the bone screw 700 and the sharpened edge may be an edge 760 on the end of the fenestration 730 closest to a tip of the bone screw 700. In other contemplated embodiments, the sharpened edge may be an edge 762 of a fenestration 730 oriented in a longitudinal direction along the length of the bone screw 700.

While the surfaces of the fenestration forming the edge 750 are shown in FIGS. 7A-7E as being generally planar surfaces, in other embodiments, one or both of the surfaces may be otherwise contoured. For example, surface 754, surface 756, or surface 758 may all be curved (e.g., concave) surfaces in other contemplated embodiments.

While the fenestrations 730 having the edges 750 are shown as being formed in a threaded bone screw, in other contemplated embodiments, the fenestrations 730 including the edges 750 may be formed in threadless fasteners (e.g., nails, tacks, pins, etc.).

Figure 8:
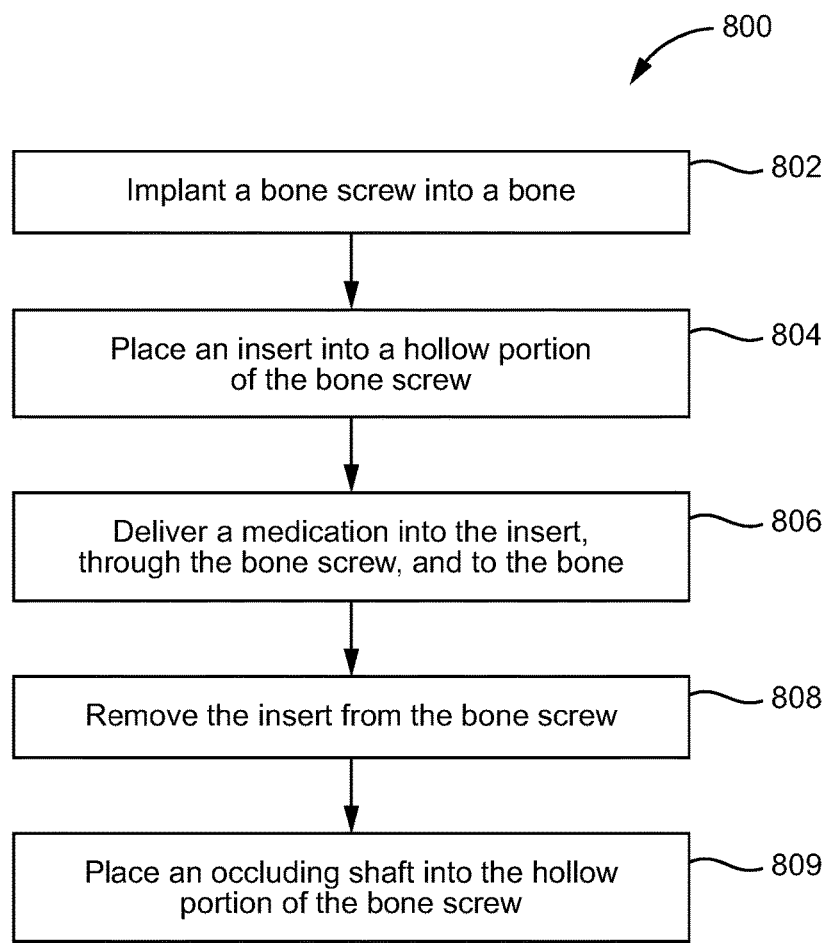
FIG. 8 is a flowchart of a method for utilizing a bone screw and bone screw insert to deliver a medication, in accordance with an exemplary embodiment.

Referring now to FIG. 8, a method 800 of administering a substance to a bone is shown according to an exemplary embodiment. First a cannulated, fenestrated bone screw is introduced (e.g., implanted) into a bone (step 802). A cannulated insert is then inserted into the hollow portion of the bone screw (step 804). A substance such as a medication is then delivered into the cannulated portion of the insert so that the substance is delivered through the bone screw and to the bone (step 806). Under some circumstances, one may find it advantageous to introduce the insert into or along the bone screw, in its entirety or only partially, prior to introducing the bone screw into the bone. This sequence might be preferred in order to shorten the overall surgery time, or to reduce the amount of material that enters the bone screw fenestrations from outside the screw during screw insertion, for example. Alternately, other circumstances may make it more advantageous to introduce the insert into the bone screw, in its entirety or only partially, after the bone screw is introduced into the bone. This latter sequence might be preferred in order to determine which screw fenestrations or exterior insert attachment mechanisms (e.g. grooves) are located at the optimum location for delivery of the desired substance, and thus what insert configuration or length should be used to facilitate substance delivery to desired locations in or near a bone. Other sequences can be envisioned by one skilled in the art, such as for example, partially introducing the bone screw into a bone, partially or completely inserting the insert into or along the bone screw, and then completing the insertion of the bone screw into the bone. Even more sequence variations are possible when one considers the additional step of introducing the substance into the cannulated portion of the bone screw insert, and all such sequence variations are to be included within the scope of this disclosure.

In certain procedures, the insert may be removed from the bone screw after use. For example, the insert may be utilized for facilitating the delivery of a substance such as a drug to a portion of the bone adjacent to the bone screw and the method 800 may further include removing the insert from the bone screw (step 808). An occluding shaft may then be inserted into the hollow portion of the bone screw (step 809).

Figure 9:
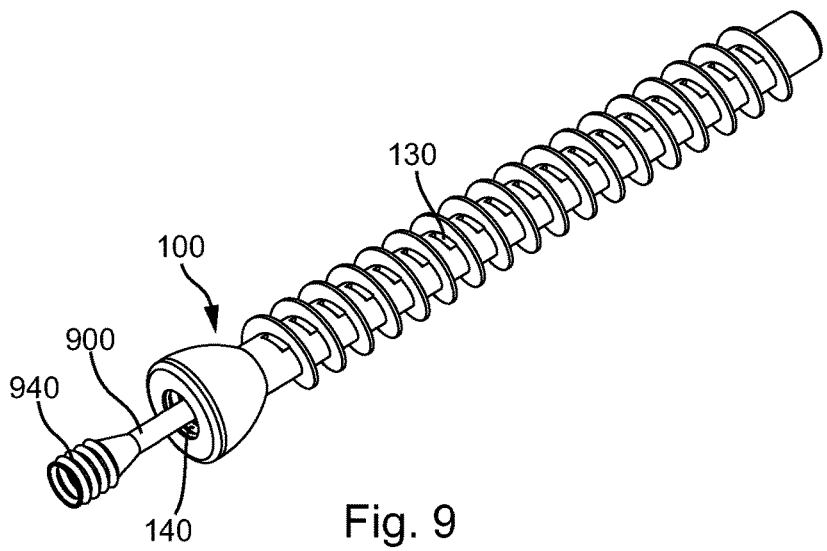
FIG. 9 is a perspective view of a bone screw and an occluding shaft, in accordance with an exemplary embodiment.

Referring to FIG. 9, in accordance with one embodiment, an occluding shaft 900 is similar in shape and size to the insert 300 but is instead a solid body or a hollow body lacking any fenestrations or other openings. The occluding shaft 900 is instead configured to obstruct the fenestrations 130 in the bone screw 100 to retain the medication or other substance in or around the bone and seal the open end of the bone screw 100. The occluding shaft 900 may extend the entire length of the hollow portion of the screw 100 or may only extend along a portion of the length of the hollow portion of the bone screw 100, forming a reservoir or cavity at the distal end of the hollow portion. One end of the occluding shaft 900 may include external threads 940 similar to threads 340 of the insert 300 that are configured to engage threads 140 in the bone screw 100.

In another embodiment, the insert may not be removed from the bone screw and an occluding shaft may be placed in the hollow cannulated portion of the insert. The occluding shaft may therefore be sized to occupy the hollow portion of the insert and may extend the entire length of the hollow portion of the insert or may only extend along a portion of the length of the hollow portion of the insert, forming a reservoir or cavity at the distal end of the hollow portion. One end of the occluding shaft may include external threads that are configured to engage internal threads in the insert.

The occluding shaft may be formed of any material compatible with the bone screw and able to be placed within the bone screw without producing adverse effects to the patient. Examples of suitable materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalcium-phosphate. Other materials useful for construction of the occluding shaft will be known to those skilled in the art.

The bone screw, insert, and occluding shaft may be sold or otherwise provided in a kit containing two or more inserts having different fenestrations or permeability characteristics. The availability of such a kit has the advantage of allowing a practitioner to select an appropriate insert based on the particular needs of the patient and including an appropriately sized occluding shaft.

Further modifications and alternative embodiments will be apparent to those skilled in the art in view of this description. Accordingly, this description is to be construed as illustrative only. The construction and arrangements of the bone screws and inserts, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A bone screw, comprising:
a shaft extending between a head of the bone screw and a tip of the bone screw, the shaft having a core diameter;
a cannulated portion formed in the shaft;
a plurality of threads extending above the core diameter;
a fenestration in the shaft providing an opening between the cannulated portion and an outer surface of the shaft;
wherein the fenestration forms a first fenestration surface on a first side of the opening and a second fenestration surface on an opposite side of the opening; and
wherein the second fenestration surface terminates at the outer surface of the shaft forming an acute angle edge directed towards the head of the bone screw, and wherein the edge protrudes from the core diameter beyond the first fenestration surface in a direction away from the cannulated portion.

2. The bone screw of claim 1, wherein the edge is configured such that the edge will assist in cutting through bone when removing the bone screw from a bone.

3. The bone screw of claim 2, wherein the fenestration comprises a longitudinal slot along a length of the shaft.

4. The bone screw of claim 3, wherein the edge is located at an end of the longitudinal slot closest to a distal end of the bone screw.

5. The bone screw of claim 1, wherein the edge is located on a side of the fenestration such that the edge will assist in cutting through bone when removing the bone screw from a bone.

* * * * *